US009872736B2

(12) United States Patent
McPherson et al.

(10) Patent No.: US 9,872,736 B2
(45) Date of Patent: *Jan. 23, 2018

(54) SURGICAL APPARATUS INCLUDING A HAND-ACTIVATED, CABLE ASSEMBLY AND METHOD OF USING SAME

(71) Applicant: Medtronic, Inc., Minneapolis, MN (US)

(72) Inventors: Cameron McPherson, Frisco, TX (US); Rex W. Shores, Norfolk, MA (US); Mitchell Sherry, Fort Worth, TX (US)

(73) Assignee: Medtronic, Inc., Minneapolis, MN (US)

( * ) Notice: Subject to any disclaimer, the term of this patent is extended or adjusted under 35 U.S.C. 154(b) by 863 days.

This patent is subject to a terminal disclaimer.

(21) Appl. No.: 14/188,041

(22) Filed: Feb. 24, 2014

(65) Prior Publication Data

US 2014/0171992 A1 Jun. 19, 2014

Related U.S. Application Data

(63) Continuation of application No. 10/930,646, filed on Aug. 31, 2004, now Pat. No. 8,657,808.

(51) Int. Cl.
*A61B 17/00* (2006.01)
*A61B 19/00* (2006.01)
(Continued)

(52) U.S. Cl.
CPC .......... *A61B 19/56* (2013.01); *A61B 17/1615* (2013.01); *A61B 17/1626* (2013.01);
(Continued)

(58) Field of Classification Search
CPC ............ A61B 17/1615; A61B 17/1617; A61B 17/1626; A61B 17/32; A61B 17/320758;
(Continued)

(56) References Cited

U.S. PATENT DOCUMENTS 4,835,509 A 5/1989 Yoshino et al.
5,136,220 A 8/1992 Philipp
(Continued)

FOREIGN PATENT DOCUMENTS

DE 2820437 A1 7/1979
JP 2002345843 A 12/2002
(Continued)

OTHER PUBLICATIONS

European Examination Report dated Jun. 26, 2007 in European Application No. 05009372.3-1526.
(Continued)

*Primary Examiner* — Gregory Anderson
*Assistant Examiner* — Sarah Simpson
(74) *Attorney, Agent, or Firm* — Harness Dickey

(57) ABSTRACT

A surgical apparatus and method according to which a cable assembly is connected to a handpiece and includes a sensing element, and a member adapted to move relative to the sensing element to control the operation of a motor in the handpiece.

20 Claims, 2 Drawing Sheets

(51) Int. Cl.
*A61B 17/16* (2006.01)
*A61B 17/32* (2006.01)
*A61B 17/3207* (2006.01)
*A61B 34/00* (2016.01)

(52) U.S. Cl.
CPC ...... *A61B 17/32* (2013.01); *A61B 17/320758* (2013.01); *A61B 34/25* (2016.02); *A61B 2017/00017* (2013.01); *A61B 2017/00022* (2013.01); *A61B 2017/00367* (2013.01)

(58) Field of Classification Search
CPC .......... A61B 2017/00017; A61B 2017/00022; A61B 2017/00367; A61B 34/25
See application file for complete search history.

(56) References Cited

U.S. PATENT DOCUMENTS

| | | | |
|---|---|---|---|
| 5,365,155 A | | 11/1994 | Zimmermann |
| 5,690,618 A | | 11/1997 | Smith et al. |
| 5,712,543 A | | 1/1998 | Sjostrom |
| 5,720,742 A | | 2/1998 | Zacharias |
| 5,867,082 A | | 2/1999 | Van Zeeland |
| 6,017,354 A | * | 1/2000 | Culp ................... A61B 90/98 604/22 |
| 6,120,462 A | * | 9/2000 | Hibner ............... A61B 10/0275 600/566 |
| 6,520,976 B1 | | 2/2003 | Gage |
| 7,247,161 B2 | | 7/2007 | Johnston et al. |
| 8,657,808 B2 | | 2/2014 | McPherson et al. |
| 2001/0007944 A1 | | 7/2001 | Mark et al. |
| 2002/0087179 A1 | | 7/2002 | Culp et al. |
| 2004/0172015 A1 | | 9/2004 | Novak |
| 2005/0085838 A1 | * | 4/2005 | Thompson ......... A61B 10/0275 606/170 |
| 2005/0096661 A1 | | 5/2005 | Farrow et al. |
| 2006/0020258 A1 | | 1/2006 | Strauss et al. |
| 2006/0047272 A1 | | 3/2006 | McPherson et al. |

FOREIGN PATENT DOCUMENTS

| | | |
|---|---|---|
| WO | WO-9920187 A1 | 4/1999 |
| WO | WO-03079911 A1 | 10/2003 |

OTHER PUBLICATIONS

U.S. Appl. No. 10/930,646, filed Aug. 31, 2014, now U.S. Pat. No. 8,657,808.

* cited by examiner

SURGICAL APPARATUS INCLUDING A HAND-ACTIVATED, CABLE ASSEMBLY AND METHOD OF USING SAME

CROSS-REFERENCE TO RELATED APPLICATIONS

This application is a continuation of U.S. patent application Ser. No. 10/930,646 filed on Aug. 31, 2004. The entire disclosure of the above application is incorporated herein by reference.

FIELD

This invention relates to a surgical apparatus including a hand-activated, cable assembly, and to a method of using same.

BACKGROUND

This section provides background information related to the present disclosure which is not necessarily prior art.

Many tools for use in surgical procedures take the form of a handpiece driven by an electric motor to which a cutting accessory, such as a drill bit, bur, saw blade, reamer, and the like, is attached, for removing or separating sections of body tissue.

A hand-activated control switch is usually provided on the handpiece and a sensing element is provided in the handpiece and cooperates with the switch to generate a signal representative of the position of the switch. The signal is sent to a console that converts the available line voltage into a voltage signal and sends the signal to the motor of the handpiece to power the motor.

However, these types of arrangements are not without limitations. For example, if the sensing element within the handpiece fails prematurely, then hand-activation of the handpiece is not possible until it is repaired. Also, the switch is designed to work with only those handpieces that have a sensing element in the handpiece, and handpieces that do not have an imbedded sensing element cannot be used with a hand-activated control switch. Moreover, if the sensing element is in the form of a Hall-effect sensing element that detects the proximity of a magnet in or on the lever, the sensing element could be inadvertently activated if the handpiece were placed on or near a magnet or a magnetic surface.

The publication listed in Table 1 below is hereby incorporated by reference herein in its entirety. As those of ordinary skill in the art will appreciate readily upon reading the Summary of the Invention, Detailed Description of the Preferred Embodiments and Claims set forth below, many of the devices and methods disclosed in the publication of Table 1 may be modified advantageously by using the teachings of the present invention. TABLE-US-00001 TABLE 1 Patent/Publication No. Published Date Inventor 2002/0087179 A1 Jul. 4, 2002 Jerry A. Culp, et al.

SUMMARY

This section provides a general summary of the disclosure, and is not a comprehensive disclosure of its full scope or all of its features.

In order to overcome the above problems, and according to an embodiment of the present invention, a surgical apparatus is provided that includes a sensing element and a switch incorporated in a cable assembly that connects to a handpiece and to a console. The cable assembly can be used with a variety of handpieces, and, if the sensing element fails prematurely, the handpiece is not rendered inoperable, but rather the cable assembly can simply be replaced with a new one. Also, a Hall-effect sensing element can be used without running the risk of inadvertently activating the sensing element if the handpiece were placed on or near a magnet or a magnetic surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3-6 are views similar to that of FIG. 2 but depicting alternate embodiments of the component of FIG. 2. Corresponding reference numerals indicate corresponding parts throughout the several views of the drawings.

DETAILED DESCRIPTION

Example embodiments will now be described more fully with reference to the accompanying drawings.

Figure 1:
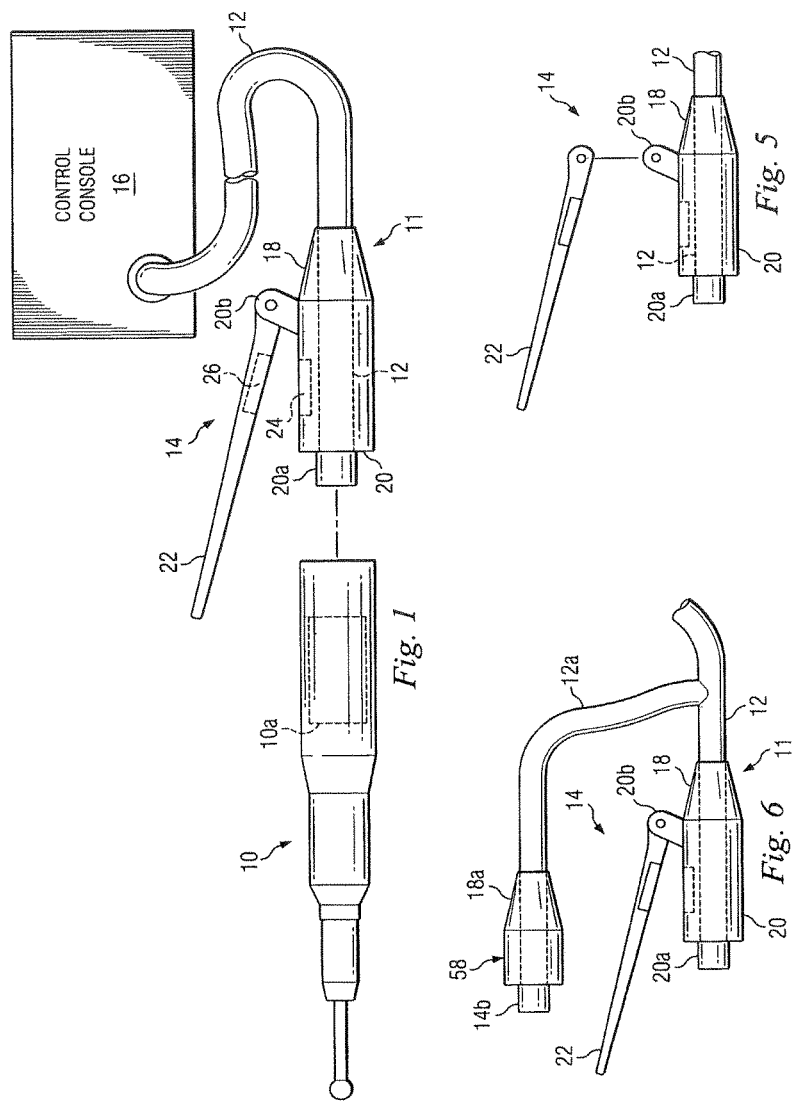
FIG. 1 is an exploded isometric view of an embodiment of the present invention.

Referring to FIG. 1 of the drawings, the reference 10 refers, in general, to a handpiece in the form of a powered tool for use in surgical procedures. The handpiece 10 is driven by an internal motor 10*a*, and is adapted to receive a cutting accessory, such as a drill bit, a bur, a saw blade, a reamer, or the like, that can be removably connected to the output shaft of the motor 10*a*. When the motor 10*a* is activated in a manner to be described, the output shaft and therefore the cutting accessory are rotated at a predetermined speed for removing or separating sections of body tissue.

A cable assembly 11 is provided that includes a cable 12, one end of which is electrically and mechanically connected to the handpiece 10 in a manner to be described. The cable assembly 11 also includes a switch/sensing element device 14 extending over the latter end portion and adapted to be activated and to control the handpiece 10, also in a manner to be described.

The other end of the cable 12 is electrically and mechanically connected to a console 16 that contains electrical circuitry that converts the available line voltage into a drive signal suitable for driving the motor 10*a*. A conventional, conically-shaped, strain relief sleeve 18 extends from the device 14 and over the corresponding portion of the cable 12.

The device 14, when manually actuated under conditions to be described, produces signals that are transmitted, via the cable 12, to the console 16. The console 16 responds to these signals and, in turn, produces the above drive signals that are transmitted to the motor 10*a*, via the cable 12, and through the device 14 to the motor 10*a*.

The device 14 includes a cylindrical housing 20 that extends around the corresponding end portion of the cable 12. A male electrical plug, or jack, 20*a* extends from one end of the housing 20 and is connected to the corresponding end of the cable 12 and engages a corresponding female socket (not shown) provided in the corresponding end of the handpiece 10 (FIG. 1). It is understood that the cable 12 includes one or more electrical conductors that extend into the other end of the housing 20 and are connected in a manner to be described.

The device 14 also includes a lever 22 pivotally mounted between two spaced mounting flanges extending from the housing 20, with one of the flanges being referred to by the reference numeral 20b. It is understood that a biasing member (not shown), such as a leaf spring or the like, can be provided that biases the lever in a direction away from the housing 20 and provides resistance to movement towards the housing, in a conventional manner.

Figure 2:
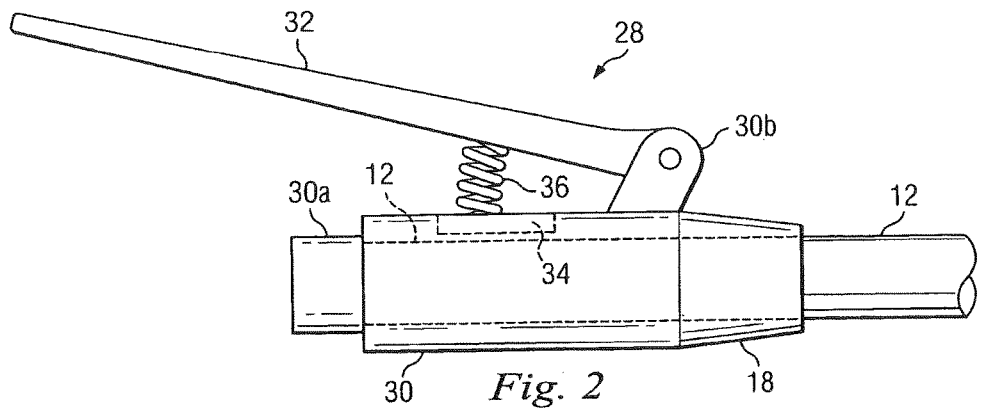
FIG. 2 is an enlarged elevational view of a component of the embodiment of FIG. 1.

A Hall-effect sensing element 24 is disposed in the housing 20 with the upper surface of the sensing element extending flush with the upper surface of the housing, as viewed in FIG. 2. A magnet 26 is provided in the lever 22 in alignment with the sensing element 24, with the lower surface of the magnet extending flush with the lower surface of the lever. The sensing element 24 is conventional and, as such, responds to movement of the lever 22, and therefore the magnet 26, proximate to the sensing element, and outputs a corresponding signal, as will be described in detail. When the lever 22 is released, the above-mentioned leaf spring forces it back to its original position.

The cable 12 (FIG. 1) contains a plurality of electrical conductors (not shown) that are electrically connected to the console 16 and extend from the console to the housing 20, where one or more of the conductors are electrically connected to the sensing element 24 in the housing 20 and one or more are electrically connected to the jack 20a of the housing for connection to the motor 10a. Thus, a signal emitted by the sensing element 24 is transmitted to the console 16, causing a drive signal to be transmitted from the console to the motor 10a to drive the motor. Preferably the latter signal is in the form of a DC voltage that can vary, depending on the position of the magnet relative to the sensing element, to enable the speed of the motor 10a to be varied accordingly.

In operation, the surgeon attaches a cutting tool to the handpiece 10 and uses his finger to manually push, or force, the lever 22 towards the housing 20 so that the magnet 26 approaches the sensing element 24. The sensing element 24 is calibrated to output a signal when the magnet 26 gets within a predetermined distance of the sensing element, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor 10a and enables the speed of the motor to be varied, depending on the position of the magnet relative to the sensing element 24, as discussed above.

An alternate embodiment of the device 14 is referred to, in general, by the reference numeral 28 in FIG. 2 and includes a housing 30 having a male electrical plug, or jack, 30a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 30 and are connected in a manner to be described.

The device 28 also includes a lever 32 is pivotally mounted between two spaced mounting flanges extending from the housing 30, with one of the flanges being referred to by the reference numeral 30b.

A strain gauge 34 is disposed in the housing 30 with the upper surface of the strain gauge extending flush with the upper surface of the housing, as viewed in FIG. 2. The strain gauge 34 is conventional and, as such, is calibrated to respond to a predetermined force exerted on it and to output a corresponding signal, as will be described in detail.

A helical compression spring 36 extends between the latter surface and the upper surface of the strain gauge 34 so as to normally urge the lever away from the housing 30. When the lever 32 is manually pivoted towards the housing 30, it exerts a force on the spring 36, which compresses the spring and, in turn, exerts a force on the strain gauge 34. When the lever 32 is released, the spring forces it back to its original position.

The cable 12 (FIG. 1) contains a plurality of electrical conductors (not shown) that are electrically connected to the console 16 and extend from the console to the housing 30, where one or more of the conductors are electrically connected to the sensing element strain gauge 34 in the housing 30, and one or more are electrically connected to the jack 30a of the housing for connection to the motor 10a. Thus, a signal emitted by the strain gauge 34 is transmitted to the console 16, causing a signal to be transmitted from the console to the motor 10a to drive the motor. Preferably the latter signal is in the form of a DC voltage that can vary, depending on the force exerted on the strain gauge 34, to enable the speed of the motor 10a to be varied accordingly.

In operation, the surgeon attaches a cutting tool to the handpiece 10 and uses his finger to manually push, or force, the lever 32 towards the housing 30 against the force of the spring 36 so that a corresponding force is exerted on the strain gauge 34. The strain gauge 34 is calibrated to output a signal when the latter force reaches a predetermined value, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor and enables the speed of the motor to be varied, depending on the force exerted on the strain gauge 34, as discussed above.

Figure 3:
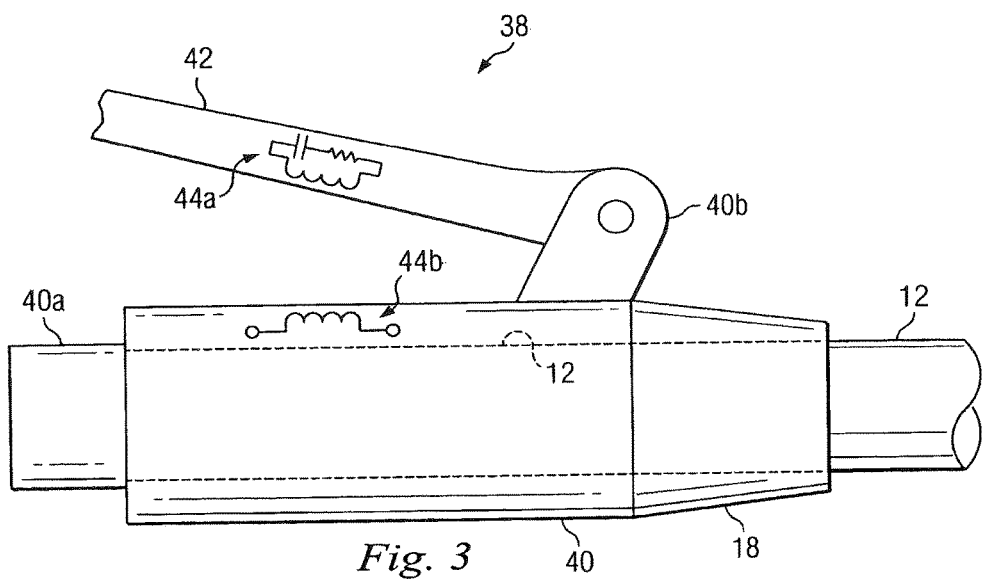

Another alternate embodiment of the device 14 is referred to, in general, by the reference numeral 38 in FIG. 3 and includes a housing 40 having a male electrical plug, or jack, 40a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 40 and are connected in a manner to be described.

The device 38 also includes a lever 42 pivotally mounted between two spaced mounting flanges extending from the housing 40, with one of the flanges being referred to by the reference numeral 40b. It is understood that a biasing member (not shown), such as a leaf spring or the like, can be provided that biases the lever 42 in a direction away from the housing 40 and provides resistance to movement towards the housing in a conventional manner.

One portion 44a of an inductively coupled circuit is mounted in the lever 42 and another portion 44b of the circuit is mounted in the housing 40 and in alignment with the circuit portion 44a. The circuit portion 44a is in the form of a resonant circuit (RLC) and the circuit portion 44b includes an inductor. Thus, the circuit portion 44a interacts with the circuit portion 44b to induce an output signal voltage in the circuit portion 44b when the circuit portion 44a is within a predetermined distance of the circuit portion 44b as a result of the lever 42 being pivoted towards the housing 40. When the lever 42 is released, the above-mentioned leaf spring forces it back to its original position.

The cable 12 (FIG. 1) contains a plurality of electrical conductors (not shown) that are electrically connected to the console 16 and extend from the console to the housing 40, where one or more of the conductors are electrically connected to the circuit 44b in the housing 20, and one or more are electrically connected to the jack 40a of the housing for connection to the motor 10a. Thus, a signal emitted by the assembly 38 in the above manner is transmitted to the console 16, causing a signal to be transmitted from the console to the handpiece motor 10a to drive the motor. Preferably the latter signal is in the form of a DC voltage that can vary, depending on the relative positions of the circuit portions 44a and 44b, to enable the speed of the motor 10a to be varied accordingly.

In operation, the surgeon attaches a cutting tool to the handpiece 10 and uses his finger to manually push, or force, the lever 42 towards the housing 40. The inductively coupled circuit portions 44a and 44b are calibrated to output a signal when the lever 42, and therefore the circuit portion 44a, gets within a predetermined distance of the circuit portion 44b in the housing 40, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor 10 and enables the speed of the motor to be varied, depending on the relative positions of the circuit portions 44a and 44b, as discussed above.

Figure 4:
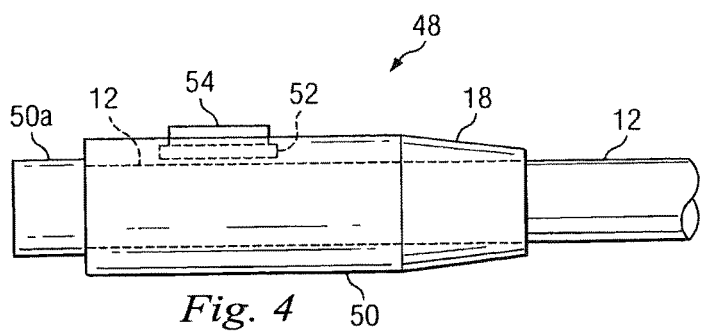

Another alternate embodiment of the device 14 is referred to, in general, by the reference numeral 48 in FIG. 4 and includes a housing 50 having a male electrical plug, or jack, 50a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 30 and are connected in a manner to be described.

The device 14 also includes a strain gauge 52 disposed in an opening in the housing 50 with the upper surface of the strain gauge extending slightly below the upper surface of the housing, as viewed in FIG. 5. The lower portion of a manually-actuatable button 54 also extends in the latter opening over the strain gauge 52, with the lower surface of the button in contact with the upper surface of the strain gauge 52. The upper portion of the button 54 projects outwardly from the upper surface of the housing 50 so that it can be manually engaged, or pressed.

The strain gauge 52 is conventional and, as such, responds to a force exerted on it by a manual pressing of the button 54 downwardly as viewed in the drawing, and is calibrated to output a corresponding output signal. In this context, it is understood that the button 54 is conventional, and, as such, includes a mechanism to return it to its previous position after being pushed downwardly in the above manner.

The cable 12 (FIG. 1) contains a plurality of electrical conductors (not shown) that are electrically connected to the console 16 and extend from the console to the housing 50, where one or more of the conductors are electrically connected to the strain gauge 52 in the housing 50 and one or more are electrically connected to the jack 50a of the housing for connection to the motor 10a. Thus, a signal emitted by the assembly 48 in the above manner is transmitted to the console 16, causing a signal to be transmitted from the console to the handpiece motor 10a to drive the motor. Preferably the latter signal is in the form of a DC voltage that can vary, depending on the position of the magnet relative to the sensing element, to enable the speed of the motor 10a to be varied accordingly.

In operation, the surgeon attaches a cutting tool to the handpiece 10 and uses his finger to manually push or force the button 54 towards the strain gauge 52 to exert a force on the strain gauge 52. The strain gauge 52 is calibrated to output a signal when the latter force reaches a predetermined value, and the signal is transmitted to the console 16, via the corresponding conductors in the cable 12.

The above-mentioned electrical circuitry in the console 16 responds to the signal received from the device 14, and generates a drive signal that is passed to the motor 10a, via the corresponding conductors in the cable 12. The signal drives the motor 10a and enables the speed of the motor to be varied, depending on the amount of force exerted on the strain gauge 52 by the button 54.

It is understood that the embodiments of FIG. 1 can be modified according to FIG. 5, in which the lever is removable from its pivotal engagement between the flanges, including the flange 20b, on the housing 20. This can be done in any conventional manner such as by providing a pin (not shown) that can be inserted through aligned openings in the flanges and the lever to provide the pivotal connection, yet can be quickly removed- to permit removal of the lever. This enables the surgeon to eliminate the finger control capability provided by the device 14.

It is understood that the levers 32 and 42 of the embodiments of FIGS. 3 and 4, respectively, can also be removable in the above manner.

The embodiment of FIG. 6 also provides the surgeon the option of eliminating the finger control capability provided by the device 14. In this embodiment the end portion of the cable 12 is bifurcated to form an additional portion 12a, and a male electrical plug, or jack, 58 is affixed to the end of the latter portion that mechanically and electrically engages a corresponding female socket (not shown) provided in the corresponding end of the handpiece 10 (FIG. 1). A strain relief sleeve 18a, identical to the sleeve 18, is provided that extends from the jack 58 and over the corresponding portion of the cable portion 12a.

Thus, if the surgeon wants finger control capability of the motor 10a, he can plug the jack 20a of the housing 20 into the handpiece 10 in the manner discussed above; or, if not, he can plug the jack 58 into the handpiece.

It is understood that the cable portion 12a can also be provided in the embodiments of FIGS. 2-5.

Since, in each of the above embodiments the sensing element and switch are both incorporated in the cable assembly 11, the cable assembly can be used with a variety of handpieces. Also, if the sensing element fails prematurely, the handpiece is not rendered inoperable, but rather the cable assembly 11 can simply be replaced with a new one. Further, in the embodiment of FIG. 2 there is no risk of inadvertently activating the sensing element 24 if the handpiece were placed on or near a magnet or a magnetic surface.

Variations

It is understood that several variations may be made in the foregoing without departing from the scope of the invention. For example, the levers and the push button in the above embodiments are interchangeable and could be replaced by toggle switches or finger/button interfaces. Further, sensing elements other than the ones described above can also be used. Moreover, the console can be eliminated if it is not necessary to house the above-described electrical circuit. Also, the output shaft of the motor 10a can be oscillated, reciprocated, or the like, rather than rotated, as discussed above. Moreover, the motor 10a can be in the form of a pneumatic motor, or the like.

The preceding specific embodiments are illustrative of the practice of the invention. It is to be understood that other expedients, known to those skilled in the art or disclosed herein, may be employed without departing from the invention or the scope of the appended claims. For example, the present invention is not limited to surgical instruments employing a cutting element, but may find further applications in which a relatively small instrument is powered from an external console.

In the following claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system, comprising:
   a cable assembly comprising:
      a cable housing separate from and configured to be selectively and removably connected to a handpiece having a motor that drives a surgical tool;
      a sensing element housed in the cable housing to generate a signal;
      at least one conductor extending from the cable housing and configured to transmit the signal;
      a switch member moveable relative to the sensing element by manual operation of a user; and
      a signaling member fixed to the switch member and moveable with the switch member relative to the sensing element;
      wherein the sensing element housed within the cable housing generates the signal based at least on a position of the signaling member relative to the sensing element by movement of the switch member relative to the cable housing.

2. The system of claim 1, further comprising:
   a control separate from and connected to the cable assembly to control the motor based on the signal from the sensing element.

3. The system of claim 2, further comprising:
   the handpiece separate from the cable housing having a housing that encloses at least the motor that is configured to operate the surgical tool received by the handpiece;
   wherein the motor receives an operation signal from the control based on the signal from the sensing element.

4. The system of claim 3, wherein the sensing element housed in the cable housing that is selectively coupled to the handpiece allows the operation signal from the control to reach the motor.

5. The system of claim 4, wherein the switch member includes at least one of a lever pivotally coupled to the cable housing or a button moveably coupled to the cable housing.

6. The system of claim 4, where the cable housing includes a male connector configured to be selectively received in a female socket of the handpiece.

7. The system of claim 4, further comprising:
   the surgical tool connected to the handpiece.

8. A system, comprising:
   a handpiece having a handpiece housing to be grasped by a user;
   an electric motor housed in the handpiece housing and configured to be driven by a drive signal from a separate external controller;
   a connecting portion of the handpiece configured to be selectively and removably coupled to an external and separable cable assembly having a sensing element that generates a control signal sent to the external controller; and
   a tool connecting portion formed by the handpiece housing to connect to a tool to be operated by the electric motor.

9. The system of claim 8, further comprising:
   the cable assembly comprising:
      a cable housing,
      the sensing element fixed to the cable housing to generate the control signal,
      a signaling member moveable relative to the sensing element, and
      a conductor to conduct the control signal; and
   the external controller connected to the cable assembly to receive the control signal.

10. The system of claim 9, wherein the sensing element is selected from one of a strain gauge, an inductively coupled circuit, a pressure gauge, or a Hall-effect sensing element.

11. The system of claim 10, wherein the external controller is configured to generate the drive signal based on the control signal to operate the electric motor in the handpiece.

12. The system of claim 10, further comprising:
   a cable connector formed by the cable housing.

13. The system of claim 12, wherein the cable connector is a male connector and the connecting portion is a female socket.

14. The system of claim 9, further comprising:
   the tool connected to the tool connecting portion of the handpiece and operated by the electric motor.

15. A method of controlling a handpiece having a motor and connected to a control console, comprising:
   connecting a first end of a cable to a cable housing of a cable assembly that is separate from and configured to be removably connected to the handpiece;
   positioning a sensing element within the cable housing;
   connecting a switch with the cable housing configured to be moved relative to the sensing element within the cable housing;
   connecting a signaling member to the switch; and providing a connector at an end of the cable housing to removably connect the cable assembly to the handpiece;

wherein the sensing element is configured to generate a sensing signal based at least on a position of the signaling member relative to the sensing element within the cable housing by movement of the switch relative to the cable housing.

16. The method of claim 15, further comprising:
connecting a second end of the cable to the control console.

17. The method of claim 16, further comprising:
operating the switch to selectively generate an operating signal by the control console.

18. The method of claim 17, further comprising:
generating the sensing signal based upon a position of the signaling member relative to the sensing element within the cable housing; and
receiving the sensing signal at the control console.

19. The method of claim 18, further comprising:
providing the handpiece with the motor that is controlled with the operating signal; and
removably connecting the cable housing to the handpiece.

20. The method of claim 19, further comprising:
operating a tool connected to the handpiece with the motor by operation of the switch and sensing element.

* * * * *